United States Patent
Rupp

[11] Patent Number: 5,451,428
[45] Date of Patent: Sep. 19, 1995

[54] METHOD FOR PRETREATING THE SURFACE OF A MEDICAL DEVICE

[75] Inventor: Lothar Rupp, Aixheim, Germany

[73] Assignee: Hewlett-Packard Company, Palo Alto, Calif.

[21] Appl. No.: 861,325

[22] Filed: Mar. 31, 1992

[30] Foreign Application Priority Data

May 21, 1991 [EP] European Pat. Off. ............ 91108146

[51] Int. Cl.$^6$ ........................... B05D 3/06; A61F 2/00
[52] U.S. Cl. ...................... 427/2.12; 427/2.25; 427/488; 427/491; 427/534; 427/255.2
[58] Field of Search ................ 427/2, 488, 489, 491, 427/509, 520, 534, 535, 2.12, 2.24, 255.2, 2.25

[56] References Cited

U.S. PATENT DOCUMENTS

| | | | |
|---|---|---|---|
| 4,072,928 | 2/1978 | Lidel | 427/509 |
| 4,193,138 | 3/1980 | Okita | 3/1.4 |
| 4,326,532 | 4/1982 | Hammar | 427/419.7 |
| 4,743,258 | 5/1988 | Ikada et al. | 427/255.6 |
| 4,810,784 | 3/1989 | Larm | 536/20 |
| 4,897,433 | 1/1990 | Sugo et al. | 427/2 |
| 4,919,659 | 4/1990 | Horbett et al. | 623/1 |
| 4,921,723 | 5/1990 | Nichols et al. | 427/488 |
| 4,987,181 | 1/1991 | Bichon et al. | 525/54.1 |
| 5,002,582 | 3/1991 | Guire et al. | 427/2 |
| 5,007,928 | 4/1991 | Okamura et al. | 427/491 |
| 5,034,265 | 7/1991 | Hoffman et al. | 427/2 |
| 5,053,048 | 10/1991 | Pinchuk | 427/2 |
| 5,080,924 | 1/1992 | Kamel et al. | 427/2 |
| 5,134,192 | 7/1992 | Feijen et al. | 427/2 |
| 5,152,783 | 10/1992 | Suzuki et al. | 427/2 |
| 5,244,654 | 9/1993 | Narayanan | 427/2.25 |
| 5,246,451 | 9/1993 | Trescony | 427/2.25 |
| 5,258,041 | 11/1993 | Guire | 427/2.25 |

FOREIGN PATENT DOCUMENTS

| | | |
|---|---|---|
| 0124200 | 11/1984 | European Pat. Off. . |
| 0294905 | 12/1988 | European Pat. Off. . |
| 0348690 | 3/1989 | European Pat. Off. . |
| 0352199 | 1/1990 | European Pat. Off. . |
| WO87/00060 | 1/1987 | WIPO . |
| WO89/11919 | 12/1989 | WIPO . |

Primary Examiner—Diana Dudash

[57] ABSTRACT

A method for pretreating the surface of a medical device, and of applying a biological coating in a further step, uses the plasma polymerization technique or the plasma grafting technique. A functional monomer, i.e. a monomer with a functional group, or a mixture of a pure monomer and a substance which can provide the required functional groups under spark discharge or under the influence of charge carriers, results in a polymer coating with free functional groups which may react with the biological coating to provide optimum adhesion of the biological coating. The process is carried out in a pressure-tight chamber with an inlet for the functional monomer under low pressure and electromagnetic radiation provided by a radiation source.

17 Claims, 4 Drawing Sheets

Fig. 7
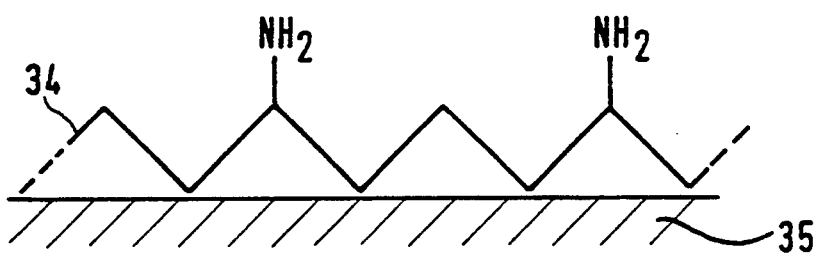
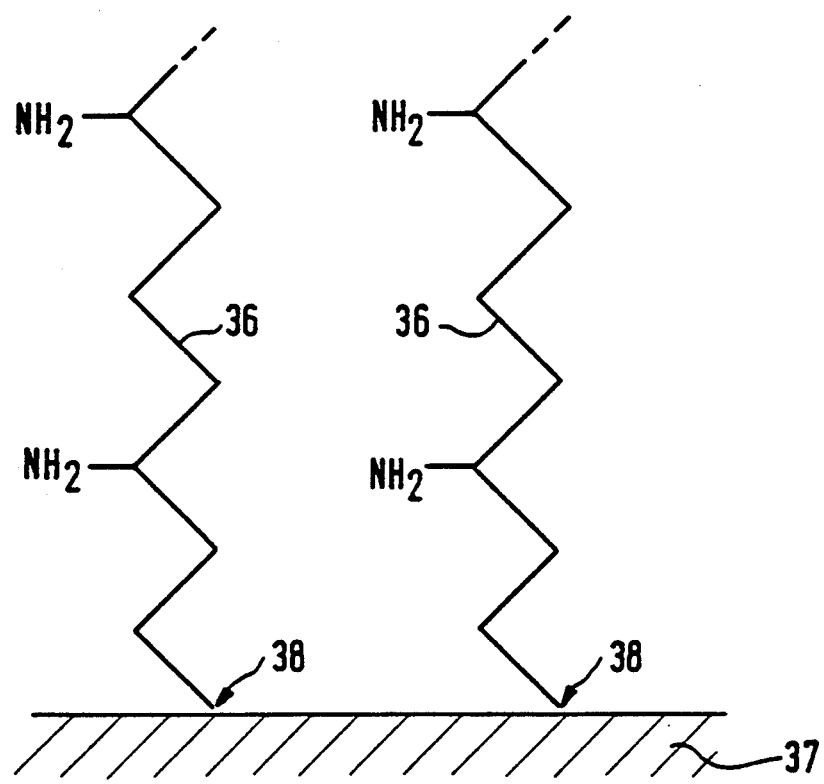
Fig. 8

METHOD FOR PRETREATING THE SURFACE OF A MEDICAL DEVICE

METHOD FOR PRETREATING THE SURFACE OF A MEDICAL DEVICE

The present invention relates to a method of pretreating the surface of a medical device for a biological coating and applying a biological coating to the surface of such medical device.

BACKGROUND OF THE INVENTION

A common problem in medical devices intended for blood contact is the biocompatibility of the surface of such devices. Medical devices such as artificial heart valves are often in permanent or at least long-lasting contact with blood. This does not only apply to medical devices implanted or otherwise introduced into the human or animal body, but also to medical devices used in extracorporeal systems like a heart-lung machine. If no special care is taken, the contact between the medical device and the blood may result in so-called "clotting" (coagulation) at the surface of the medical device. Such clots may render the medical device (e.g. a sensor) inoperable. Clots can also reduce the free cross-sectional area of a blood vessel, therefore reducing blood flow. Perhaps most dangerously, a clot formed on the surface of the medical device may be detached by flowing blood and be transported by the blood flow into a position where it can occlude a blood vessel, (in particular, a capillary) thus causing thrombosis.

The situation is even more critical in case of a catheter or an intravascular blood gas sensor introduced in a blood vessel of relatively small diameter such as the radial artery or the femoral artery. The catheter may be completely blocked by a clot, so that the blood pressure cannot be measured or that no blood samples can be taken. In case of an intravascular blood sensor, the active area may be blocked, and no fresh blood can reach the sensor. The above considerations are of particular importance when long-term contact between the medical device and the blood is intended. Even with optimum material selection for the medical device, clotting cannot be reliably prevented.

A common approach to solve this problem, i.e. to prevent the formation of clots, is to coat the medical devices with a biological coating (sometimes also referred to as bioactive or antithrombogenic coating). Coatings suited for this purposes are well-known in the art. For example, a heparin-based coating, such as described in U.S. Pat. No. 4,810,784, may be used. Other suitable biocompatible materials are e.g. phosphorylcholine (EP-B-157 469) or polyester (U.S. Pat. No. 4,792,599). Hirudin may be used as well. Other biological coating materials useful as anticoagulants are known in the art.

A common problem when applying such biological coatings to a medical device is to ensure reliable adhesion between the coating and the surface of the medical device, i.e. reliable immobilization of the coating. It is understood that poor adhesion would lead to detachment of the coating so that the medical device loses its antithrombogenic properties. As the biological coating does not adhere to the surface of the medical device by itself, additional measures have to be taken. Further, it has to be ensured that the biological coating does not lose its bioactive properties during the immobilization process.

A known solution to this problem is to coat the surface of the medical device with a polymer and to apply the biological coating to the polymerized surface. For this purpose, the uncoated medical device is put into a polymer bath, i.e. a solvent containing dissolved polymer. When the medical device is removed, its surface carries a thin film of solvent containing the polymer. The solvent then vaporizes, such that the pure polymer resides on the surface of the medical device. Subsequently, the biological coating is applied, e.g. by putting the medical device into an appropriate bath. However, the immobilization of a biological coating fastened on the surface of a medical device in this manner is not always reliable.

The inventor in the present case has particularly noted that parts of the biological coating detached in use from an intervascular blood gas sensor. This has particularly happened when a medical device is stored or deposited in a liquid for a longer time period (e.g. an intravascular sensor requiring a wet or liquid environment to keep its operability even when not in use). Such detachment is an intolerable disadvantage of the known technique, partially because of the danger for the patient as blood clots may attach to the uncoated portions of the surface, and partially as such removal of the biological coating may affect the measuring accuracy of the sensor where parts of it are coated and others are not.

SUMMARY OF THE INVENTION

It is therefore a major objective of the present invention to provide a method for reliable attachment of a biological coating to the surface of a medical device. According to one embodiment of the invention, the method for pretreating the surface of a medical device comprises the steps of:

1. The medical device is exposed to a chemical agent consisting of monomer molecules which are chemically combined with functional groups. The chemical agent is at least in its gaseous state.

2. Electromagnetic waves are irradiated into the chemical agent and/or onto the surface of said medical device until the molecules of the chemical agent constitute a functional polymer on the surface of the medical device.

3. The biological coating is applied to the polymerized monomer surface of the medical device.

BRIEF DESCRIPTION OF THE DRAWINGS

FIG. 7 shows a schematic drawing of the coated surface by the current invention of plasma polymerization.

FIG. 8 shows a schematic drawing of the coated surface by the plasma grafting technique.

DETAILED DESCRIPTION OF PREFERRED EMBODIMENTS

Figure 1:
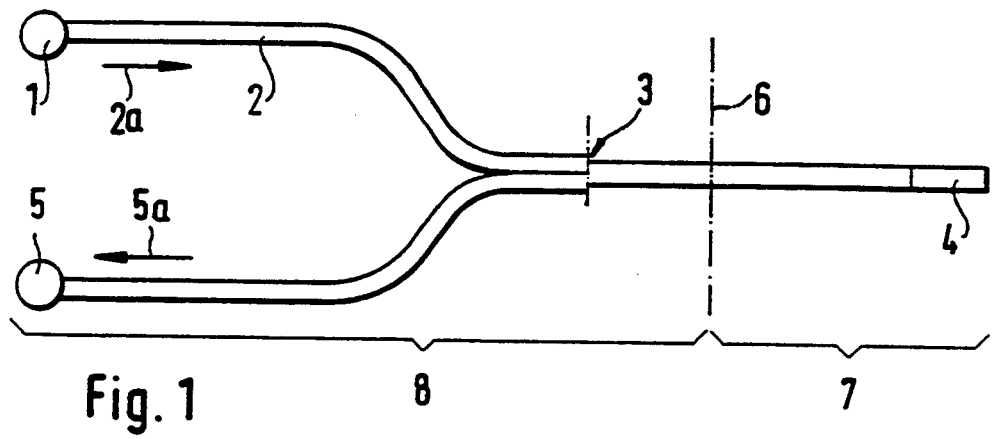
FIG. 1 shows a schematic drawing of an intravascular blood gas measuring system.

The invention makes use of a technique which is known as "plasma polymerization." According to this technique, the object to be coated with a polymer is put in a pressure-tight chamber. Monomers in gaseous form are then conducted into the chamber. A source of electromagnetic radiation irradiates high-frequency waves into the chamber, thereby creating a plasma (i.e. a gas containing free radicals). Even during spark discharge, temperature in the chamber is only slightly increased. The plasma thus created allows the monomers to polymerize on the surface of the object. The polymer forms a thin layer on the surface, just like a very thin hose or tube.

In the light of the unsatisfying results obtained with the above-described technique of applying dissolved polymers to the surface of the medical device, the inventor has investigated usual (e.g. thermal) polymerization techniques such as thermolysis, photolysis and use of radical starters. Although no polymer molecules are applied to the surface by these techniques, monomers are polymerized. This could be an attractive approach as the single polymer molecules are more effectively "muddling," thus leading to increased consistency. However, even these usual polymerization techniques did not produce a satisfying result. Attempts with the above described plasma polymerization technique resulted in limited success.

The inventor has found that the desired effect can be achieved if monomers with an additional functional group are used instead of single monomers. In fact, plasma polymerization of monomers with a functional group resulted in a coating which was able to keep the biological coating very reliably in place. Studies have shown that the biological coating does not detach from polymers produced in this way even after long-term use. The present invention thus overcomes the disadvantages of the prior art. In particular, medical devices coated with a first polymer coating according to the invention and a second biological coating have proven to operate very accurately. Their operation is not impaired by either of the coatings. For example, this is important for medical sensors since the sensor reading should not be influenced by either coating. Still, the biological coating does adhere to the surface of the medical device over very long time periods, so that thrombosis and other negative effects are avoided. This is particularly due to the functional groups of the polymer which adhere chemically to the biological coating. "Functional polymer" as used herein means a polymer with functional groups.

Further, the biological coating is able to resist considerable mechanical stress. The invention is not only suited for intravascular gas sensor, but also a variety of other medical devices intended for blood contact, such as artificial blood vessels, heart valves, catheters and the like. Intravascular blood gas sensors as such are basically known in the art, see e.g. EP-B-279 004, EP-B-336 984 and EP-A-336 985. The full content of these publications is hereby incorporated into the disclosure of the present invention by reference.

In the case of an intravascular blood gas sensor, the "plasma" coating generated by the current method has further advantages. In particular, such a sensor consists of a variety of materials, e.g. the coating of the single sensors, the semipermeable membranes covering their diffusion zones, a sheath etc., which are all in blood contact. Therefore, if the biological coating would be directly applied to the sensor, it would cover areas of different consistency and different physical properties. It could thus happen that the biological coating does not behave in a uniform manner. For example, its resistance to the accumulation or adhesion of clots could be varying dependent on the covered material, or it could detach from certain areas only and remain on other areas. The latter effect is particularly disadvantageous as a limited detachment of several square micrometers is difficult to detect, but still dangerous for the patient. These problems and disadvantages are overcome by the present invention because it is now possible to provide a uniform and reliable polymer coating so that the biological coating adheres to a uniform material.

It is a further advantage of the current method that it can be implemented very easily and in a cost-effective manner. This is because a basically known apparatus can be used to effect plasma polymerization. The only basic modification is the use of monomers with an additional functional group.

Plasma Polymerization Technique

To apply the polymer coating, the medical device is put in a closed, preferably pressure-tight chamber. The gaseous chemical agent consisting of monomer molecules chemically combined with functional groups is then allowed to stream into the chamber through an appropriate opening or valve. Next, a source of radiation energy is switched on. This source may be arranged at a side wall of the chamber or in an annular arrangement around the chamber which preferably has a cylindrical cross section. Other suitable arrangements of the radiation source may be used as well. Because of the high intensity of the radiation, an electrically shielded chamber is preferred. In an advantageous embodiment, the emitted electromagnetic waves are in the radio frequency spectrum. Specifically, a frequency of 13.56 Mhz has been used. The electromagnetic waves are irradiated into the chamber, and the spark discharge causes the gaseous chemical agent to form a "plasma", e.g. a gas with free radicals This allows the monomers with their respective functional groups to form a polymer which covers the surface of the medical device.

The biological coating may then be applied to the polymer-coated surface in basically known manner. The polymer-coated medical device may be removed from the chamber and then put into a chemical bath in order to apply the biological coating. It is even not necessary that the step of applying the biological coating is performed immediately after the appliance of the polymer coating. Instead, the biological coating may be applied weeks later.

The appliance of the polymer coating and the biological coating are chemically separate steps. Therefore, the present invention does not only relate to the combination of applying a polymer coating and a biological coating, but also to a method for pretreating the surface of a medical device. That is, it relates to the steps necessary to apply a layer of monomers with functional groups in preparation of the appliance of the biological coating itself.

The process of plasma polymerization may be significantly improved by the use of a pressure below atmospheric pressure. This can be achieved by a pressure-tight chamber which is approximately evacuated. Advantageously, the pressure is reduced until it is in a range from 0.01 millibar to 10 millibar, and more specifically, in a range from 0.1 millibar to 1 millibar. In one embodiment of the invention, a pressure of 0.3 millibar ($3.10^{-4}$ bar) has been applied to the chamber, for a duration of around 20 minutes and with a RF (radiation frequency) power of 30 W (watts), with excellent results.

As outlined above, the used chemical agent that is preferably used consists of monomers incorporating functional groups. The wording "monomer molecules chemically combined with functional groups" as used herein means that each or at least the majority of monomer molecules is combined with or bound to at least one functional group. Monomers as the basis for polymerization as such are well-known in the art. A common basic structural formula for monomers is:

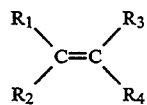
(1)

wherein $R_1$, $R_2$, $R_3$, and $R_4$ denote hydrogen atoms, halogen, or organic residues. See for example, Alfred Kemper/Rüdiger Fladt, Chemie, Stuttgart 1968, p. 290.

According to the present invention, the used monomers are further chemically combined with functional groups. Such functional groups are at least partially kept during the plasma coating process and result in a functional polymer which can covalently bind to other molecules. In a general sense, a functional group is a chemically active or reactive group which is responsive to substitution or rearrangement, and more specifically, a functional group can be defined as a group which has a tendency for amide formation, amine formation, acid formation, esterification, etherification etc.

There are several functional groups which have been found advantageous. A preferred group is e.g. the amine group, —$NH_2$. Each monomer molecule may be combined with one or more amino groups. It is understood that further groups, radicals etc. may also be chemically bound to such a functional monomer. A typical useful chemical agent consisting of a monomer and an amino group, a functional monomer is allylamine, $H_2C=CH—CH_2—NH_2$. The surface of the medical device polymerized with allylamine comprises free amino groups which in turn may bind to the molecules of the biological coating. Another chemical agent of this kind is 4-amino-1-butene, $H_2C=CH—CH_2—CH_2NH_2$. It is understood that other olefins with additional amino groups are advantageous as well. In general, it is expressed as $H_2C=CH—(CH_2)_n—NH_2$, where $n=0,1,2,...n$. Instead of using an olefin with appended amino group, it is also possible to use a pure olefin and to add ammonia, $NH_3$. That is, a physical mixture of these substances is used rather than a chemical compound. Such a mixture produces a polymer coating with free amino groups on the surface of the medical device with even better yield than produced by unsaturated amines.

Another useful functional group is the carboxyl group, —COOH. The respective chemical agents are therefore preferably unsaturated carboxylic acids, e.g. acrylic acid ($H_2C=CH—COOH$), butenoic acid ($H_2C=CH—CH_2—COOH$), pentenoic acid ($H_2C=CH—CH_2—CH_2—COOH$), and so on. The general chemical formula for such unsaturated carboxylic acids is $H_2C=CH—(CH_2)_n—COOH$ where $n=0,1,2,...n$.

The —OH group as such has also been found to be suited as functional group. A typical chemical agent of this kind is allyl alcohol, $H_2C=CH—CH_2—OH$. The general group of alcohols useful for the present invention can be given by the formula $H_2C=CH—(CH_2)_n—OH$ where $n=0,1,2,...n$.

It should be noted that the above formula (1) does not cover all possible types of monomers. For example, a monomer with triple bond, i.e. a monomer with the general structural formula:

could be used in the present invention as well. An example of such a monomer with additional functional group (in this case, an amino group) is $HC=C—CH_2—NH_2$ (3-amino-1-propine); the general notation for the class of amino compounds of this type is $HC=C—(CH_2)_n—NH_2$ where $n=0,1,2,...n$.

The most general definition of a monomer is a substance which is able to polymerize. Formulae (1) and (2) are thus limited generalizations only and do not cover all possible types of monomers.

It will be appreciated that the examples of chemical agents, monomers with functional groups described above, although they have been proven very useful for the present invention, relate to preferred embodiments only, and that the skilled man may be able to identify other chemical agents, monomers or functional groups suited for this invention. The above examples illustrate that there is a large variety of chemical agents, even of basically different constitution, fulfilling the needs of the invention.

It will further be appreciated that, instead of applying a chemical agent consisting of monomer molecules chemically combined with functional groups to the surface of the medical device, it is also possible to apply the pure monomer and to accomplish its desired chemical composition with a functional group in the plasma, i.e. under electromagnetic radiation. In this case, a substance has to be added to the pure monomer which is able to form a functional group under radiation. The substance then combines with the pure monomer. The chemical agent referred to above is thus created in situ as an intermediate product which then reacts in the described manner, i.e. by forming a functional polymer on the surface of the medical device. That is, although the process is started with a physical mixture instead of a chemical compound, its result, and even the second step, are the same as if a chemical composition were used.

One example of this kind has already been described above. This was the physical mixture of a pure olefin and ammonia, which then forms a chemical compound with an —NH$_2$ group under the influence of radiation. Other substances which may be physically added to the monomer are e.g. carbon dioxide (CO$_2$) in case a carboxyl group is intended to be chemically bound to the monomer as an intermediate product, or water (H$_2$O) in case the intermediate product should comprise an —OH group. Other such substances useful to create suitable functional groups are available to one of ordinary skill.

Plasma Grafting Technique

In an alternative embodiment of the invention, the so-called plasma grafting technique is used in contrast to the plasma polymerization technique. This technique comprises two basic steps: In the first step, a chemically inert gas such as a noble gas such as argon, helium or neon is applied to the medical device, and the source of electromagnetic radiation is turned on. This creates or induces charge carriers on the surface of the medical device. These charge carriers remain present even when the source of radiation is switched off.

In the second step, the medical device is exposed to a chemical agent of the same constitution as in the plasma polymerization technique. If the process is performed in a closed chamber, the inert gas is removed by suction, and the chemical agent is allowed to stream into the chamber. However, in this second step, the source of electromagnetic radiation or the spark discharge is switched off. The charge carriers in the outer layers of the surface of the medical device initiate the polymerization process.

The major advantage of the plasma grafting technique is that the ends of several polymer chains are covalently bound to the surface of the medical device. That is, there is a chemical bonding not only between the polymer coating and the biological coating, but also between the surface of the medical device and the polymer coating. This further reduces the probability that the biological coating, with or without polymer coating, may detach from the surface of the medical device.

Another advantage of the plasma grafting technique is that shorter polymer chains are created. The monomers do not or hardly polymerize among each other, but on the surface of the medical device only so that the process is more effective.

It is understood that a physical mixture of a pure monomer and a substance which is able to form the required functional group during or just immediately prior to the polymerization process may also be used when performing the plasma grafting technique. However, a slight distinction to the plasma polymerization technique has to be noted in this case. The functional monomer consisting of monomer molecules with additional functional group is formed during the second step of the plasma grafting process in situ, i.e. when the radiation source is switched off. This means that a monomer and a substance have to be used which are able to combine chemically under the influence of the charge carriers created in the first step (appliance of inert gas and spark discharge), instead as under spark discharge as in the plasma polymerization technique. However, most monomers and substances used in the plasma polymerization technique may also be used for the plasma grafting technique, and one of ordinary skill will be able to identify further suited substances.

Prior Purifying Step

In an advantageous embodiment, a further method step is added to the plasma polymerization technique or the plasma grafting technique. This further steps as performed prior to any of the polymerization steps. It consists of exposing the medical device to a chemically active (aggressive) gas such as oxygen and switching the source of radiation on. During spark discharge impurities such as dust or residues left by fingerprints etc. are sparked until the surface of the medical device is substantially clean from such impurities. The additional step of cleaning the surface has the further advantage that additional charge carriers are created on the outer surface of the medical device. However, in contrast to the plasma grafting technique, the charge carriers created during the purifying process recombine quite quickly as soon as the radiation source is switched off and the purifying gas (chemically active gas) is removed. This effect may be prevented by flushing the purifying gas out with the inert gas so that the purifying gas is immediately replaced by an inert gas.

One may imagine that the above process steps may be combined in any suitable manner depending on the equipment and the requirements of the application. For example, the plasma polymerization technique may be used with or without prior purifying step. Further, the plasma grafting technique may or may not be combined with the purifying step. In a preferred embodiment, incorporating the plasma grafting technique with prior purification, the inventive method comprises therefore three different steps of the process:

1. Apply chemically active gas (e.g. oxygen), switch on radiation—the surface of the medical device is purified by sparking, and temporary charge carriers are created in the outer surface.

2. Flush the chemically active gas out by an inert gas (e.g. argon) while the radiation source is still operating—the temporary charge carriers created during step 1 are thus made "quasi-permanent," i.e become charge carriers with a considerably longer lifetime, and further charge carriers are created.

3. Flush the inert gas out with a functional monomer (monomer with functional groups), switch off source of radiation—the charge carriers in the outer surface of the medical device start the polymerization. By the way, the inert gas may also rarify the functional monomer.

As outlined above, step 3 could be replaced by flushing with a mixture of a pure monomer and a substance, such as ammonia, so that the functional monomer is created just prior to polymerization in situ.

Biological Coating

It is a goal of all the various techniques described above to establish a functional polymer coating on the surface of the medical device which is able to chemically react with the biological coating, i.e. to have the functional groups of the polymer bind to certain molecules of the biological coating. A method of binding heparin to —NH$_2$ groups is described in the above-mentioned U.S. Pat. No. 4,810,784 wherein the amino groups are reacted with "fragment" heparin carrying a terminal aldehyde group to a Schiffs base, which is then, by reduction, converted to a secondary amine. It has to be noted that the results of this prior art technique are not always reliable if no further measures are taken. This may be caused by the fact that functional polymers are directly (i.e. without polymerization) applied to the surface of a device by vaporizing the solution in which the polymer is dissolved as described above.

Another approach to bind the biological coating to the surface with functional polymer is esterification. Such binding process may be useful if the biological coating is based on phosphorylcholine. Two —OH groups of the polymer coating and of the biological coating are esterified by binding to each other whilst a $H_2O$ group is removed. A further possibility to bind the biological coating to the polymer coating is acid amide formation. For the purpose of illustration, how a polyallylamine as the functional polymer may bind to phosphorylcholine as biological coating is given here:

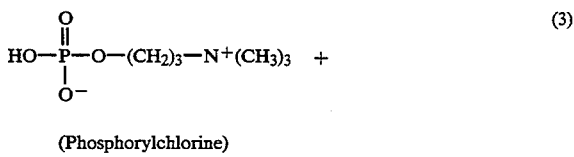

(Phosphorylchlorine)

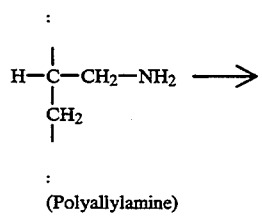

(Polyallylamine)

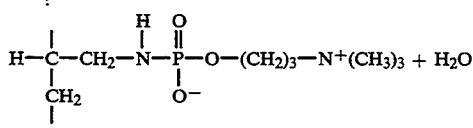

People skilled in the art will be aware of further suitable mechanisms suited for the specific biological coating used.

In general, the biological coating may be applied to the polymer coating according to any prior art technique. This has particularly the advantage that, in order to practice the present invention, not the complete coating process has to be adapted, but only the plasma polymerization step may be adapted.

As will already be apparent from the foregoing, several functional groups are useful to fulfill the need of the present invention. What is, in general, required is a chemically active group, i.e. a group which is responsive to substitution or rearrangement. Suitable mechanisms include amide formation, amine formation, esterification, etherification, etc. For example, any halogen group would be suited as a functional group, whereas a methyl group would not be.

An important, but not strictly required, property of the present invention is that the functional groups bound to the monomers are stable even after the plasma polymerization or grafting process. For example, the —$NH_2$ group of the created functional polymer does not react with other chemical substances after the plasma coating process. Therefore, it is possible to apply the biological coating at a later point in time or even at a different location. This makes the process and the handling easier.

The invention also relates to an apparatus for performing the method according to the present invention. In general, most components of the apparatus are elements commonly used to perform plasma polymerization or plasma grafting. However, a container has to be provided filled with a chemical agent consisting of monomer molecules chemically combined with functional groups. Such chemical agent has to be present at least in its gaseous state, wherein said container is lockably connected with said chamber. The locking means may be a valve. In this combination, the required functional monomer may be provided to the reaction or discharge chamber. Further containers may be provided for a chemically active gas for the purification step or for an inert gas for plasma grafting.

According to another preferred embodiment of the present invention, a shelf or rack in said chamber is provided for suspending or hanging of medical devices. This is particularly useful if intravascular blood gas sensors have to be coated. The sensors should not be in contact with the walls of the chamber in order to provide a complete coating on their whole surface.

The present invention further relates to the use of a chemical agent consisting of monomer molecules chemically combined with functional groups, or of a monomer mixed with a substance which, under the influence of electromagnetic radiation or of charge carriers, forms a functional group which binds chemically to said monomer for pretreatment of a medical device prior to appliance of a biological coating.

Example

FIG. 1 depicts a system for the invasive measurement of blood parameters including the partial carbon dioxide pressure ($pCO_2$) or the PH value. The light of an optical transmitter 1 is directed into an optical fiber 2 (see arrow 2a). Preferably, this is a glass fiber. Usually a train of light pulses is used, but this is not a strict requirement. The light passes an optical coupler 3 and reaches tip 4 of the sensor. Tip 4 is intended for introduction into the artery of a patient and contains a gel into which a dye such as phenol red is immobilized. Said dye modifies at least one optical parameter, preferably the intensity, of the light depending on the $pCO_2$ (or, in other cases, the $pO_2$ or the pH) value of the blood. The modified light is reflected into the same fiber and, after passing through optical coupler 3, reaches an optical receiver 5 (see arrow 5a). It is understood that optical transmitter 1 and optical receiver 5 are incorporated in a monitor or other measuring instrument. Dashed line 6 indicates a releasable connection between the probe 7 and the monitor 8. The optical probe consists of a multiplicity of sensors and the related number of optical fibers; preferably, it comprises 3 sensors responsive to $pO_2$, $pCO_2$ and pH.

Figure 2:
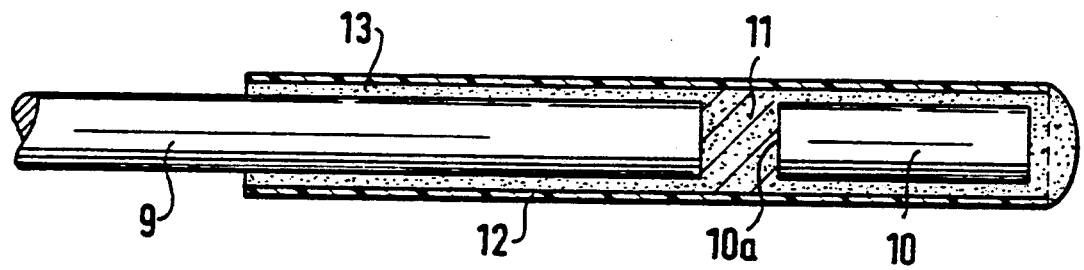
FIG. 2 is a longitudinal section of a single sensor forming part of a probe in the intravascular blood gas measuring system.

Operation of a single sensor will now be explained by means of FIG. 2, which shows a longitudinal section through a pH sensor. The mechanical construction of the pH sensor is typical for sensors of this type. The $pO_2$ and the $pCO_2$ sensor have a similar construction. According to FIG. 2, the pH sensor comprises a glass fiber 9 and an optical reflector 10. Optical reflector 10 is made of stainless steel. Between the optical fiber 9 and the reflector 10, a gel 11 is located. This gel is used to immobilize a dye such as phenol red whose optical characteristics vary with the blood parameter. In this case, pH is to be measured. The surface 10a of the optical reflector 10 facing the gel 11 is polished.

The sensor is surrounded by a semi-permeable or selective membrane 12 which is fastened on the sensor by means of a glue 13. As FIG. 2 depicts, the glue is only introduced at the distal end of the sensor (left side in FIG. 2) and at the very proximal end. The selective membrane is permeable to the ions or gas molecules to be measured. In case of the pH sensor shown in FIG. 2, the selective membrane is permeable to H+ ions.

Figure 3:
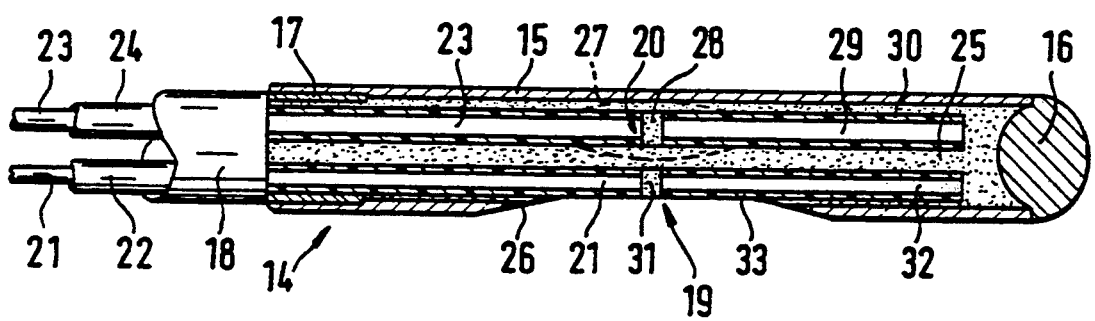
FIG. 3 is a longitudinal section of the probe tip in the intravascular blood gas measuring system.

FIG. 3 depicts a longitudinal section of the probe tip 14 of an optical probe comprising three sensors according to prior art design. A sheath 15 is closed at its outer end (proximal end) by a metal cap 16 and connected, as shown by 17, with a tubing element 18. The connection between sheath 15 and tubing element 18 is secured by adhesive means. Tubing element 18 ends (not shown) at a connector for connection to an appropriate monitor.

Sheath 15 contains three sensors. Two sensors a pH sensor 19 and a $pCO_2$ sensor 20 are shown in FIG. 3. A third sensor, namely a $pO_2$ sensor, is not shown in FIG. 3 as it is hidden behind $pCO_2$ sensor 20.

Each of the sensors is connected with the associated monitor via an optical fiber, as shown by optical fiber 21 which is surrounded by an appropriate envelope 22 for the case of pH sensor 19 in FIG. 3. Likewise, reference number 23 relates to the optical fiber of $pCO_2$ sensor 20, and reference number 24 to the envelope of this fiber.

The various sensors are fastened within sheath 15 by means of a silicone glue or adhesive 25. Sheath 15 further comprises three openings. The first opening is labeled as 26 in FIG. 3, whereas the second opening 27 is hidden behind the $pCO_2$ sensor 20. The third opening is not shown in FIG. 3; it is contained in the broken-away part. These openings ensure that, when the probe tip is introduced into a patient's artery, the sensors are in contact with the blood thus allowing gas molecules and hydrogen ions to reach the sensors.

$PCO_2$ sensor 20 further comprises a dye-containing gel 28 and an optical reflector 29. The region where dye-containing gel 28 is located is also called "diffusion zone." Sensor 20 is, insofar as contained in sheath 15, surrounded by a semi-permeable membrane 30 which is fixed on optical fiber 23 and reflector 29 by means of a further glue or adhesive. In similar manner, pH sensor 19 comprises a dye-containing gel 31, a reflector 32 and a semi-permeable membrane 33.

It is understood that the probe depicted in FIG. 3 is only a typical example for an invasive optical blood parameter probe. In other embodiments, the probe may comprise less sensors or even more elements, such as a strain relieving wire. As the probe is intended for insertion into a blood vessel, typically the arteria radialis or the arteria femoralis. Since the probe is in blood contact over several hours or even days, a biological or bioactive coating is required in order to avoid that the blood clots attach to the sensor or the surrounding catheter. Thus, a biological coating impacts the measurement or causes thrombosis.

In a specific embodiment, the probe tip or the whole sensor is exposed to an oxygen atmosphere in a pressure-tight chamber. The chamber may be part of a usual plasma polymerization or plasma grafting equipment. The pressure in the chamber is then considerably reduced to 0.7 millibar ($7.10^{-4}$ bar). Thereafter, a source of radiation is turned on for 5 minutes. The source emits RF (radio frequency) waves into the chamber. In the present embodiment, a frequency of 13.56 MHz has been used and a transmitter power of 90 W (watts). This first step sparks or "burns" impurities on the surface of the probe. Further, charge carriers are generated on the outer surface of the probe.

In a second step, argon is used to flush the oxygen out of the chamber. The radiation transmitter is still operating also at a power of 90 mW. The pressure in the chamber is further reduced to 0.2 millibar ($2.10^{-4}$ bar). The radiation source is operated for 5 minutes during this second step. The purpose of this treatment with argon under spark discharge is to create further charge carriers, and to make the charge carriers already created in the first step "quasi-permanent." When the second step is completed, the source of radiation is switched off.

In a third step, allylamine is fed into the chamber and flushes the argon out. The charge carriers in the outer surface of the probe initiate the polymerization process. The allylamine molecules polymerize on the surface of the probe but not in the gaseous environment. Due to the charge carriers on the surface, the ends of a multiplicity of the polymer chains attach to the surface so that the generated polymer coating is in "chemical" contact with the surface which in turn inhibits removal of the plasma coating. The outer ends of the polymer chains carry free and stable amino groups ($NH_2$).

The process described above is the plasma grafting process. In the case of plasma polymerization, the second step (argon flushing) is not performed, and a monomer is fed into the chamber for 20 minutes at a pressure of 0.3 millibar ($3.10^{-4}$ bar). The probe may now be removed from the chamber and coated with a biological coating in basically known manner.

Figure 4A:
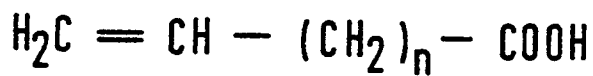
FIG. 4A shows a general formula for a carboxylic compound suitable as a chemical agent in the third step according to the current invention, wherein N is a positive integer.
Figure 4B:
FIG. 4B shows acrylic acid as a chemical agent in the third step.
Figure 4C:
FIG. 4C shows butenoic acid as a chemical agent in the third step.
Figure 4D:
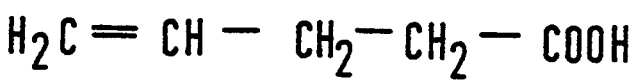
FIG. 4D shows pentenoic acid as a chemical agent in the third step.

FIGS. 4a to 4d depict a selection of suitable carboxylic compounds (monomer with carboxyl group) suitable as chemical agents in the third step. The general formula is given in FIG. 4a, wherein $(CH_2)_n$ denotes an arbitrary number of $CH_2$ groups where $n=0$ or a positive integer. FIGS. 4b to 4d respectively show acrylic acid, butenoic acid and pentenoic acid.

Figure 5A:
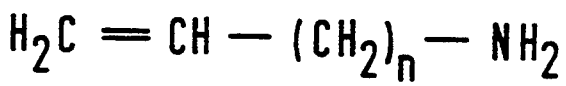
FIG. 5A shows the general formula for agents with an amino group as chemical agents of the current invention.
Figure 5B:
FIG. 5B shows allylamine as a chemical agent.
Figure 5C:
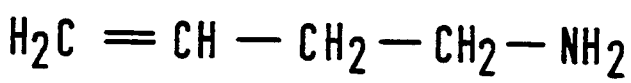
FIG. 5C shows 4-amino-1-butane as a chemical agent.

Likewise, FIG. 5a shows the general formula for agents with an amino group. Specific examples of this group of substances include Allylamine (FIG. 5b) and 4-amino-1-butene (FIG. 5c).

Figure 6A:
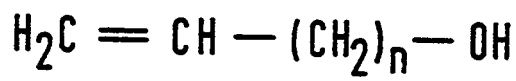
FIGS. 6A shows the general formula of suitable alcohols as chemical agents of the current invention.
Figure 6B:
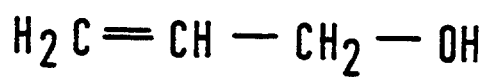
FIG. 6B shows allyl alcohol as a chemical agent.

FIG. 6a is the general formula of suitable alcohols (compounds with an —OH group). FIG. 6b depicts a typical example of this group, allyl alcohol.

FIG. 7 shows a plasma polymer 34 with free amino (—$NH_2$) groups at every 2nd carbon atom in the polymer chain on the surface 35 of an intravascular probe obtained with the plasma polymerization technique. In contrast, the result of the plasma grafting technique is depicted in FIG. 8. The ends of the plasma grafted chains 36 adhere to the surface 37 as depicted by reference number 38. This is a covalent bonding which provides better contact between polymer and surface and reduces the probability of detachment of the polymer. Further, the polymer chains in the environment of FIG. 8 are generally shorter.

Figure 9:
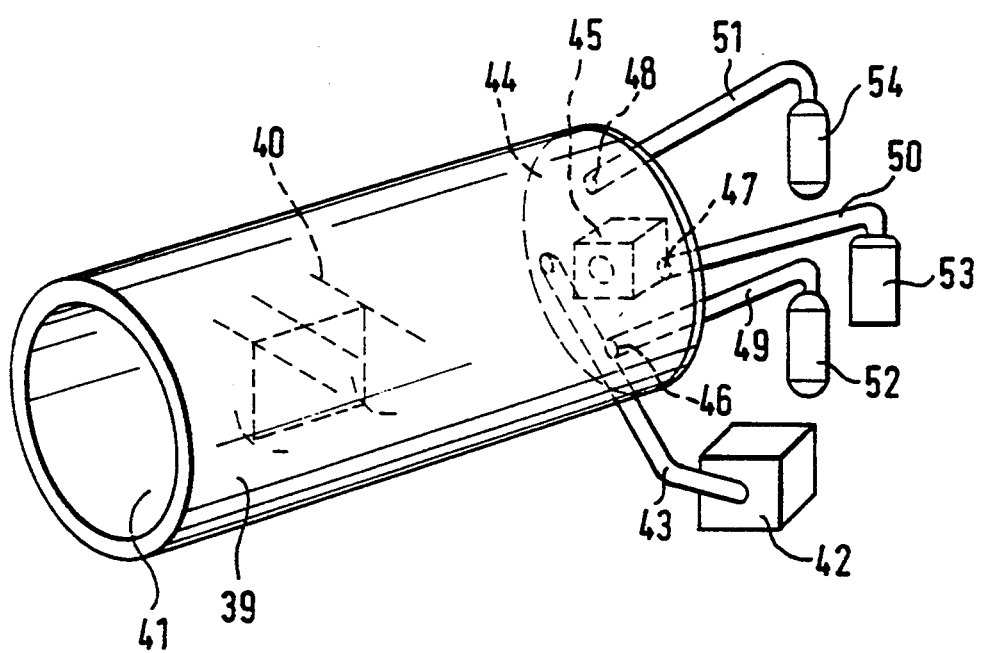
FIG. 9 illustrates a pressure-tight chamber to practice the current invention.

A basic apparatus for performing the current method is shown in FIG. 9. A pressure-tight, electrically shielded chamber 39 contains a shelf or rack 40 for pinning up of intravascular probes. The front opening 41 may be closed by a suitable door (not shown). A pump 42 is used to obtain the required low pressure. It is connected via tube 43 to back wall 44 of chamber 39. The source of radiation is depicted as 45. Three openings 46, 47 and 48 are provided as inlets for oxygen, argon and allylamine (or acrylic acid), respectively.

These openings are connected via tubes 49, 50 and 51 to respective containers 52, 53 and 54 holding these gases, or volatile liquids.

Although particular embodiments of the current invention has been shown and described, other embodiments and modifications will occur to those of ordinary skill in the art which fall within the scope of appended claims.

What is claimed is:

1. Method of coating the surface of a medical device with an anti-thrombogenic coating said method comprising the steps of:
   (a) exposing a medical device to a chemical agent which comprises a monomer;
   (b) irradiating electromagnetic waves within radio frequency range into said chemical agent toward the surface of said medical device so as to form an adhesive layer of a polymer with multiple functional groups on the surface of said medical device; and
   (c) applying the anti-thrombogenic coating to said adhesive layer of said polymer with multiple functional groups by a direct binding process selected from the group consisting of esterification, acid amide formation, amine formation and etherification.

2. Method according to claim 1 wherein said monomer is chemically combined with multiple functional groups and is present at least in its gaseous state.

3. Method according to claim 1 wherein said monomer is mixed width a substance which, under the influence of said electromagnetic waves, forms said multiple functional groups which in turn bind chemically to said monomer, said monomer being present at least in its gaseous state.

4. Method according to claim 3 wherein said monomer and said substance form said multiple functional groups which bind chemically to said monomer so as to form said polymer with multiple functional groups on the surface of said medical device.

5. Method according to claim 1 wherein said method is conducted in a closed pressure-tight chamber.

6. Method according to claim 5 wherein a pressure below atmospheric pressure is applied to said chamber until the pressure in said chamber is substantially vacuum.

7. Method according to claim 6 wherein the pressure in said chamber is in the range of $10^{-5}$ bar to $10^{-2}$ bar.

8. Method according to claim 2 wherein said monomer comprises molecules comprising at least two carbon atoms.

9. Method according to claim 8 wherein said multiple functional groups include an amino group.

10. Method according to claim 9 wherein said monomer is selected from the group consisting of allylamine, 4-amino-1-butene, any other olefin with at least one additional amino group and a combination of olefin and ammonium hydroxide.

11. Method according to claim 8 wherein said multiple functional groups include a carboxyl group.

12. Method according to claim 11, wherein said monomer is selected from the group consisting of carboxylic acids, butenoic acid and pentenoic acid.

13. Method according to claim 8 wherein said multiple functional groups include an OH group.

14. Method according to claim 13 wherein said monomer is allyl alcohol.

15. Method according to claim 1, further comprising the additional steps of:

exposing said medical device to a chemically active gas; and irradiating electromagnetic waves into said chemically active gas and onto the surface of said medical device until the surface of said medical device is substantially clean of impurities; wherein said additional steps are performed prior to exposing said medical device to said chemical agent.

16. Method according to claim 1 wherein said medical device is an intravascular blood gas sensor.

17. Method of coating the surface of a medical device with an anti-thrombogenic coating, said method comprising the steps of:
   (a) exposing a medical device to an inert gas;
   (b) irradiating electromagnetic waves within radio frequency range into said inert gas toward the surface of said medical device;
   (c) introducing a chemical agent which comprises a monomer towards the surface of said medical device so as to form an adhesive layer of a polymer with multiple functional groups the surface of said medical device; and
   (d) applying the anti-thrombogenic coating to said adhesive layer of said polymer with multiple functional groups by a direct binding process selected from the group consisting of esterification, acid amide formation, amine formation and etherification.

* * * * *